(12) United States Patent
Saunders et al.

(10) Patent No.: US 6,251,875 B1
(45) Date of Patent: *Jun. 26, 2001

(54) AQUEOUS LAXATIVE SYRUP COMPRISING LACTULOSE AND LACTITOL AND/OR MALTITOL

(75) Inventors: David Saunders, Farnham; Julita Pearson, West Wickham, both of (GB)

(73) Assignee: Xyrofin Oy, Helsinki (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/125,345
(22) PCT Filed: Feb. 6, 1997
(86) PCT No.: PCT/EP97/00543
 § 371 Date: Mar. 19, 1999
 § 102(e) Date: Mar. 19, 1999
(87) PCT Pub. No.: WO97/29755
 PCT Pub. Date: Aug. 21, 1997

(30) Foreign Application Priority Data

Feb. 19, 1996 (GB) .................................. 9603430

(51) Int. Cl.⁷ ..................................................... A61F 31/70
(52) U.S. Cl. ............................................... 514/53; 514/23
(58) Field of Search .......................................... 514/23, 53

(56) References Cited

U.S. PATENT DOCUMENTS 4,760,055 * 7/1988 Harju et al. ............................. 514/53

FOREIGN PATENT DOCUMENTS

| 0464362A1 | * 1/1992 | (EP) . |
| 464362 | 1/1992 | (EP) . |
| 2215206 | 8/1974 | (FR) . |
| 2113998 | 8/1983 | (GB) . |

OTHER PUBLICATIONS

Martindale's Extra Pharmacopocia, 29th Edition, pp. 1092–1093, 1982.

* cited by examiner

*Primary Examiner*—Elli Peselev
(74) *Attorney, Agent, or Firm*—Fitch, Even, Tabin & Flannery

(57) ABSTRACT

An aqueous laxative syrup is provided comprising one part by weight of lactulose and 0.66–1.5 parts by weight of a polyol selected from lactitol and/or maltitol. The syrup has a viscosity of 5–70 mPa.s. Preferably the polyol is lactitol. The syrup is less viscous than a lactulose-only syrup and has a pleasant balance of tastes between sweetness, acidity and bitterness. Further, it does not suffer from an overly medicinal taste. This balance of characteristics makes the syrup pleasant to take and so improves patient compliance.

13 Claims, No Drawings

AQUEOUS LAXATIVE SYRUP COMPRISING LACTULOSE AND LACTITOL AND/OR MALTITOL

The present invention relates to an aqueous laxative syrup which possesses a balance of characteristics including taste and viscosity which makes it palatable to a wide range of individuals.

The disaccharide lactulose (4-β-D-galatosyl-D-fructose) is known to be pharmacologically active as a laxative. It is 0.5–0.6 times as sweet as sucrose. Lactulose is generally marketed as a syrup because its crystallisation and drying are difficult and costly. When used to treat constipation, it is normally administered in the form of such a syrup.

Lactulose syrups which are presently marketed for the treatment of constipation or portal systemic encephalopathy (PSE) contain 620–740 g/l of lactulose. These syrups also contain about 50 g/l and 100 g/l respectively of lactose and galactose. These two sugars are by-products of the usual synthetic pathway used to produce lactulose. These sugars increase the viscosity of the syrup. Constipation is usually treated by taking 15 ml of lactulose syrup twice daily at the beginning of the treatment. This dosage is reduced according to the patient's needs. For the treatment of PSE, initially, 30–50 ml are taken three times daily, the dosage being subsequently adjusted to produce 2–3 soft stools daily.

It has been noted that patient compliance with lactulose syrups is unsatisfactory. This is firstly because such syrups are very sweet and many patients find it difficult to take a dose of three teaspoons (5 ml each) without feeling nauseous. This effect is greatly aggravated when using lactulose syrups to treat PSE, where a dose of 6–10 teaspoons has to be taken at the beginning of the treatment. In addition, lactulose syrup is relatively viscous. For instance, commercially available lactulose syrups comprising about 670 g/l have a viscosity of 230 mPa.s at 20° C. Both young and elderly patients can find such viscous syrups difficult to swallow. If the concentration of lactulose in the lactulose syrup is reduced to 500 g/l by dilution with water, then the syrup's viscosity in turn reduces to about 75 mPa.s. However, syrups of this concentration are not marketed because their dilution results in patients needing to take large-volume doses. Whilst it has been suggested to mix lactulose syrup with food or drink, medical advice is for patients to take this medicament on its own prior to a meal in order to ensure that its absorption and efficacy are not affected by food ingredients.

In summary, commercially available solutions of lactulose are highly viscous and very sweet and these factors reduce their palatability. The use of more dilute preparations, whilst solving these problems, is not satisfactory because of the need to take large volumes of the diluted solutions to obtain efficacy.

It is also known to treat constipation and PSE with lactitol. This polyol belongs to the same group of laxatives as lactulose. Lactitol (4-β-D-galactosyl-D-sorbitol) is a disaccharide sugar alcohol produced commercially by the catalytic hydrogenation of lactose. Lactitol crystallises in several anhydrous and hydrous crystalline forms, but it is usually marketed as a powder of its most stable monohydrate form.

The British National Formulary, No. 27 (March 1994) indicates that for the treatment of constipation, 20 g of lactitol should be taken initally as a daily single dose, and that this amount should be subsequently adjusted so that one stool is produced daily. This amount is increased to 50–70 g daily for the treatment of PSE. Lactitol may be administered by mixing its powder directly into a meal. It may also be taken as a solution by dissolving in water. A solution formed from 670 g of lactitol per liter of water has a viscosity of 23 mPa.s at 20° C. Accordingly, lactitol solutions have a significantly lower viscosity than lactulose syrups comprising an equivalent concentration of lactulose. In addition, lactitol is not as sweet as lactulose, being around 0.35 times as sweet as sucrose. Thus, lactitol does not suffer from the main disadvantages of lactulose when used as a laxative.

Some patients however find lactitol solutions to have imperfect palatability as they perceive them to have a somewhat acidic, bitter and medicinal taste. Accordingly, the problem remains to formulate a solution for treating constipation and/or PSE which has a balance of properties such as viscosity and taste which the vast majority of patients find acceptable.

It has also been reported that the polyol maltitol has a laxative effect. However, there is no commercial use at present of this polyol as a laxative.

EP-A-0 464 362 describes an animal feed comprising a mixture of lactitol and lactulose which promotes growth and good intestinal function. The lactulose and lactitol are present in a combined total concentration of 6.6 g/l. There is no teaching of any human application nor that the feeds have any laxative effect.

FR-A-2 215 206 describes a laxative composition comprising crystalline lactulose and crystalline sorbitol in a ratio of 1:3 to 3:1. The mixture is provided in a sachet containing 8 grams of lactulose and 8 grams of sorbitol. This mixture is dissolved in a glass of water and taken as a medicament. The resulting solution would have a combined concentration of about 150 g of lactulose and sorbitol per liter.

An object of the present invention is to provide an aqueous laxative syrup having a balance of properties providing greater palatability than presently available laxative syrups comprising either lactulose or lactitol.

According to one aspect, the present invention provides an aqueous laxative syrup having a viscosity of 5–70 mPa.s at 20° C. comprising one part by weight of lactulose and 0.6–1.5 parts by weight of a polyol selected from lactitol and/or maltitol.

Such a syrup has a lower viscosity than commercially available lactulose syrups comprising 620 g/l of lactulose or more. Such prior art syrups have a viscosity of about 185 mPa.s or more at 20° C. Further, the present syrups have a balance of flavours which renders them more palatable than laxative syrups comprising only one of lactulose and lactitol.

The syrups of the present invention may be prepared by mixing commercially available lactulose syrups with a solution formed by dissolving lactitol in water, so that the resulting syrup has appropriate relative concentrations of both lactulose and lactitol. The resulting syrup has a lower viscosity than a correspondingly concentrated solution of lactulose and a slightly greater viscosity than a correspondingly concentrated solution of lactitol.

It is preferred that the syrup should comprise 1 part by weight of lactulose and 0.8–1.2 parts by weight of the polyol. More preferably, the syrup should comprise 1 part by weight of lactulose and about 1 part by weight of the polyol.

The above aqueous laxative syrup may be prepared in a form suitable for immediate oral administration, or in a form suitable for administration after dilution with water. An aqueous syrup for immediate oral administration as a laxative preferably comprises a total of 500–800 g, more preferably 600–700 g, and most preferably about 666 g, of both lactulose and the polyol per liter.

It is preferred that the solvent in which the lactulose and polyol are dissolved is water. This may however contain other pharmacologically acceptable solvent components such as a small amount of ethanol.

In all of the above embodiments, it is preferred that the polyol is lactitol only.

According to a further aspect of the invention, the use is provided of water, lactulose and a polyol selected from lactitol and/or maltitol for the manufacture of an aqueous laxative syrup comprising 1 part by weight of lactulose and 0.66–1.5 parts by weight of the polyol.

In such a use, it is preferred that the resulting laxative syrup should have a viscosity of 5–70 mPa.s at 20° C. The resulting laxative syrup also preferably has all of the preferred features previously described.

It will be evident that viscosity is an important characteristic of the aqueous laxative syrup provided by the present invention. Such viscosity can be measured using a system supplied by Haake and which uses a CH temperature controller. The basic unit of this system is an RV20 Rotovisco rheometer. This unit is controlled using an RC20 Rheocontroller with version 2.4 software installed on the controlling PC system. The measuring system used is system M5. For the purpose of measuring the viscosity of syrups having a relatively low viscosity, a NV sensor system is used. All viscosities are measured at a constant temperature of 20°C.

To measure the viscosity of a solution, 10 ml is loaded into the NV cup system and the cup located in the temperature vessel. The solution is then allowed to settle in the cup and equilibrate to the desired temperature (20° C.) prior to starting the test. The solution is then subjected to a constantly increasing shear rate from $0 \text{ s}^{-1}$ to $100 \text{ s}^{-1}$. The time taken to reach this shear rate is 15 minutes. 1000 data readings are taken during this procedure. All solutions tested showed Newtonian properties under these test conditions giving acceptable regression coefficients based upon the Newtonian equation that viscosity is equal to (shear stress)/(shear rate). This calculation and data plotting are handled by the software which produces data for the regression coefficient (1.00 in all cases) and the viscosity value.

In initial tests on known lactulose syrups, the regime included a series of data points at a constantly decreasing shear rate from $100 \text{ s}^{-1}$ to $0 \text{ s}^{-1}$ in 15 minutes to evaluate any thixotropic tendencies. As none were observed, only the upward ramping slope is evaluated in the viscosity measurements.

The viscosity of a number of aqueous lactulose and/or lactitol syrups was measured using the above system, and the following results were obtained.

| Solution | Viscosity (mPa.s) |
|---|---|
| Commercial lactulose syrup comprising 670 g/l lactulose and about 150 g/l of other sugars (Comparative) | 230 |
| Diluted commercial lactulose syrup comprising 500 g/l lactulose and about 112 g/l of other sugars (Comparative) | 75 |
| 335 g/l lactitol, 335 g/l lactulose and about 75 g/l of other sugars (Invention) | 63 |
| 250 g/l lactitol, 250 g/l lactulose and about 56 g/l of other sugars (Invention) | 24 |
| 670 g/l lactitol (Comparative) | 23 |
| 500 g/l lactitol (Comparative) | 8 |

It will be seen from the above viscosity measurements that the laxative syrup of the present invention has a substantially lower viscosity than lactulose-based laxative syrups presently marketed which have a lactulose concentration of about 670 g/l. As a result of this lower viscosity, the aqueous laxative syrup of the present invention has greater palatability than the presently available laxative syrups which comprise lactulose as the principal active ingredient.

This reduction in viscosity has a further advantage that the syrups of the present invention are easier to process. Their improved flowability compared to lactulose-only syrups makes them easier to pump into bottles.

In the above tests, it is possible to replace part or all of the lactitol with maltitol which has a viscosity lower than that of lactulose. Thus, a laxative syrup comprising 335 g of lactulose and 335 g of maltitol per liter has a viscosity of 55 mPa.s.

In order to confirm the superior palatability of laxative syrups formulated in accordance with the present invention over those based only upon either lactulose or lactitol, sensory profiles of lactitol syrup, lactulose syrup and three blends of these two syrups (weight ratio of lactulose to lactitol of 25:75, 50:50 and 75:25) were established by a panel of 12 trained consumers using quantitative descriptive sensory profiling techniques. Each syrup had a total concentration of lactulose and/or lactitol of 670 g/l. The consumers employed for these assessments were selected via sensory screening tests for their sensory abilities, particularly regarding their ability to identify flavours, odours and textures, and also for good verbal communication skills. They also received training in quantitative sensory profiling methods and were experienced in profiling a wide range of food and drink products.

Tastings were designed so that panellists would consume no more than a total of 15 ml of solutions in any one tasting session only one tasting session was held on any one day. Only 5 ml of each product was available to each panellist, which was measured into a small plastic cup. Panellists took the entire 5 ml into their mouths for taste assessment. To assess the flavour of each sample, four attributes were used together with a consensus definition for each attribute. These attributes were as follows:

| Attribute Term | Consensus Definition |
|---|---|
| Sweet | One of the four basic tastes e.g. that of sucrose |
| Acid | Basic taste e.g. citric acid |
| Medicinal | Medicinal-type flavour similar to glycerin |
| Bitter | Basic taste e.g. quinine |

Six blind tasting sessions were carried out in which the panellists evaluated each product (coded) for each of the four attributes. The panellists were isolated from each other in individual tasting booths where they marked the intensity of each attribute on a linear scale. Data was collected through a computerised data collection system via a mouse and PC in each tasting booth. The following results were obtained:

| | Weight ratio of lactulose to lactitol | | | | |
|---|---|---|---|---|---|
| Flavour | 0:100 lactitol | 25:75 | 50:50 | 75:25 | 100:0 lactulose |
| Sweet | 56.5 | 52.3 | 52.8 | 55.9 | 61.0 |
| Acid | 17.2 | 19.1 | 12.1 | 14.9 | 11.9 |

-continued

| | Weight ratio of lactulose to lactitol | | | | |
|---|---|---|---|---|---|
| Flavour | 0:100 lactitol | 25:75 | 50:50 | 75:25 | 100:0 lactulose |
| Medicinal | 16.4 | 13.8 | 9.5 | 15.2 | 12.8 |
| Bitter | 12.9 | 10.8 | 6.7 | 14.1 | 9.7 |

It will be seen from the data collected that the 50:50 blend of lactulose and lactitol has a balance of flavours which is superior to either lactulose or lactitol individually, and also the other two blends tested. Thus, the 50:50 blend has a lower sweetness than both the lactulose-only solution and the lactitol-only solution; much lower acidity than the lactitol-only solution; and the lowest medicinal and bitter taste of any of the solutions tested.

Accordingly, the aqueous laxative syrups provided by the present invention have greater palatability than the previously available laxative syrups comprising only one of lactulose and lactitol. Thus, they are expected to result in improved patient compliance.

The present invention will now be further explained by way of the following Example which, whilst illustrating a preferred embodiment of the invention, should not be understood to limit it.

Example

An aqueous laxative syrup was prepared by mixing equal quantities of a standard lactulose (BP) solution comprising 670 g/l of lactulose, 50 g/l of lactose and 100 g/l of galactose, and a lactitol solution comprising 670 g/l of lactitol. The resulting aqueous laxative syrup was used to treat constipation in a patient by administering to him three 5 ml teaspoons of the syrup twice a day. The patient found the syrup to be palatable and the syrup had an efficacy comparable to that of syrups formed from only one of lactulose and lactitol.

What is claimed is:

1. An aqueous laxative syrup having a viscosity of about 5 to about 70 mPa.s at about 20° C. comprising about 1 part by weight of lactulose and about 0.66 to about 1.5 parts by weight of a polyol selected from the group consisting of lactitol and maltitol, wherein the lactulose and polyol are present in the syrup in an amount effective for use as a laxative composition.

2. An aqueous laxative syrup according to claim 1, comprising about 1 part by weight of lactulose and about 0.8 to about 1.2 parts by weight of the polyol.

3. An aqueous laxative syrup according to claim 2, comprising about 1 part by weight of lactulose and about 1 part by weight of the polyol.

4. An aqueous laxative syrup according to claim 3, comprising a total of about 500 to about 800 g of both lactulose and the polyol per liter.

5. An aqueous laxative syrup according to claim 4, comprising a total of about 600 to about 700 g of both lactulose and the polyol per liter.

6. An aqueous laxative syrup according to claim 5, comprising a total of about 666 g of both lactulose and the polyol per liter.

7. An aqueous laxative syrup according to claim 6, wherein the syrup includes water.

8. An aqueous laxative syrup according to claim 6, wherein the polyol is lactitol.

9. A method of treating constipation comprising the step of administering to a patient suffering from constipation an effective amount of an aqueous laxative syrup having a viscosity of about 5 to about 70 mPa.s at about 20° C. comprising about 1 part by weight of lactulose and about 0.66 to about 1.5 parts by weight of a polyol selected from the group consisting of lactitol and maltitol.

10. A process for producing a laxative syrup comprising blending about 1 part by weight lactulose with from about 0.66 to about 1.5 parts by weight of a polyol selected from the group consisting of lactitol and maltitol, the laxative syrup having a viscosity of from about 5 to about 70 mPa.s at about 20° C., wherein the lactulose and polyol are present in the syrup in an amount effective for use as a laxative composition.

11. The process according to claim 10 wherein about 1 part by weight lactulose is blended with about 0.8 to about 1.2 parts by weight of the polyol.

12. The process according to claim 11 wherein about 1 part by weight lactulose is blended with about 1 part by weight of the polyol.

13. The process according to claim 10 wherein the polyol is lactitol.

* * * * *